United States Patent
Ragusa

(10) Patent No.: US 9,865,025 B2
(45) Date of Patent: Jan. 9, 2018

(54) ELECTRONIC HEALTH RECORD SYSTEM AND METHOD FOR PATIENT ENCOUNTER TRANSCRIPTION AND DOCUMENTATION

(71) Applicant: Peter Ragusa, Lake Charles, LA (US)

(72) Inventor: Peter Ragusa, Lake Charles, LA (US)

( * ) Notice: Subject to any disclaimer, the term of this patent is extended or adjusted under 35 U.S.C. 154(b) by 0 days.

(21) Appl. No.: 13/687,225

(22) Filed: Nov. 28, 2012

(65) Prior Publication Data
US 2013/0138457 A1 May 30, 2013

Related U.S. Application Data

(60) Provisional application No. 61/563,857, filed on Nov. 28, 2011.

(51) Int. Cl.
*G06Q 50/24* (2012.01)
*G06Q 10/10* (2012.01)
*G06F 19/00* (2011.01)

(52) U.S. Cl.
CPC ........... *G06Q 50/24* (2013.01); *G06F 19/322* (2013.01); *G06Q 10/10* (2013.01)

(58) Field of Classification Search
CPC ......... G10L 15/26; G10L 15/22; G06Q 50/22; G06Q 50/24; G06Q 10/00; G06Q 10/06;
(Continued)

(56) References Cited

U.S. PATENT DOCUMENTS

| | | |
|---|---|---|
| 6,055,494 A | 4/2000 | Friedman |
| 6,587,830 B2 | 7/2003 | Singer |

(Continued)

FOREIGN PATENT DOCUMENTS

| | | |
|---|---|---|
| JP | 2005196394 A | 7/2005 |
| KR | 20100129016 A | 12/2010 |

OTHER PUBLICATIONS

International Search Report in International Application No. PCT/US2012/066760, dated Feb. 27, 2013, 5 pp.
(Continued)

*Primary Examiner* — Hiep V Nguyen
(74) *Attorney, Agent, or Firm* — Patterson Intellectual Property Law, P.C.; Gary L. Montle

(57) ABSTRACT

A patient encounter documentation and analytics system includes a mobile computing platform and a server-based host platform. A mobile application in tandem with a wireless microphone collects voice signals during a patient-caregiver encounter, transforms the voice signals into audio data files, and uploads the audio data files to the server. A speech recognition software module digitally transcribes the audio data file into text. A text processing module extracts and organizes relevant clinical data based on keyword, key phrase and question/answer analysis. Relevance of words and phrases may be determined in view of, e.g., their presence, frequency and context. A diagnostic decision support module enables the healthcare provider to review the determined clinical information and provide a diagnosis associated with the encounter. A documentation skeleton module extracts diagnosis-specific text components from the transcribed text file and assembles an electronic medical document based on the diagnosis and the diagnosis-specific text components.

17 Claims, 3 Drawing Sheets

(58) Field of Classification Search
CPC ............. G06F 17/30616; G06F 19/327; G06F 19/345; G06F 19/322
USPC .......................................................... 705/3
See application file for complete search history.

(56) References Cited

U.S. PATENT DOCUMENTS

| | | |
|---|---|---|
| 6,738,784 B1 | 5/2004 | Howes |
| 6,915,254 B1 | 7/2005 | Heinze et al. |
| 6,938,206 B2 | 8/2005 | Ingle et al. |
| 7,885,811 B2 | 2/2011 | Zimmerman et al. |
| 8,323,189 B2 * | 12/2012 | Tran et al. ................ 600/300 |
| 8,679,011 B2 * | 3/2014 | Islam ...................... H01S 3/302 379/106.02 |
| 2002/0019749 A1 | 2/2002 | Becker et al. |
| 2003/0227386 A1 * | 12/2003 | Pulkkinen ............ A61B 5/1113 340/573.1 |
| 2005/0038678 A1 | 2/2005 | Qian et al. |
| 2005/0055246 A1 | 3/2005 | Simon |
| 2006/0248076 A1 * | 11/2006 | Troy et al. .................. 707/5 |
| 2007/0299665 A1 | 12/2007 | Koll et al. |
| 2009/0024411 A1 | 1/2009 | Albro et al. |
| 2011/0145013 A1 | 6/2011 | McLaughlin |
| 2011/0202370 A1 | 8/2011 | Green et al. |
| 2012/0173281 A1 * | 7/2012 | DiLella et al. ................ 705/3 |

OTHER PUBLICATIONS

European Patent Office: Supplementary European Search Report regarding EP Application No. 12853915, dated May 12, 2015.

\* cited by examiner

ELECTRONIC HEALTH RECORD SYSTEM AND METHOD FOR PATIENT ENCOUNTER TRANSCRIPTION AND DOCUMENTATION

CROSS-REFERENCES TO RELATED APPLICATIONS

This application claims benefit of the following patent application which is hereby incorporated by reference: U.S. Provisional Patent Application No. 61/563,857, dated Nov. 28, 2011.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

The present invention relates generally to the generation of electronic health records. More particularly, the present invention relates to intelligent computer-implemented systems and methods for passively collecting voice data associated with caregiver-patient encounters and transforming the voice data for generation of an electronic health record with a minimal burden on the caregiver.

The United States spends more than seventeen percent of its gross domestic product (GDP) on healthcare—more than any other country. Healthcare costs are out of control, and healthcare organizations must adapt in today's business environment in order to be successful. They must be focused and efficient. Unfortunately, the vast majority of the industry remains terribly inefficient, and is only enabled by a broken healthcare delivery and reimbursement system.

Today, four-fifths of medical documentation relies on paper—in clinic and hospital forms—which is compiled into bulky charts that require significant storage space. Not only are these charts inefficient to handle, they are "dumb" and afford for nearly zero data-mining capacity. Likewise, numerous clinicians and other providers continue to rely on their memories to "store" information prior to actually documenting patient encounters.

In response, a robust healthcare information technology (HIT) has developed and electronic medical records are becoming adopted to better streamline the healthcare system and processes. However, many existing systems and methods continue to require substantial interaction on the part of the physician or other healthcare provider, meaning that not only have the beneficial effects of the technology failed to reach their potential, but that actual implementation of such systems remains relatively and undesirably low.

For example, certain systems exist which are capable of transcribing voice data associated with a medical procedure and creating an associated record, but which require the physician to follow a predetermined template or format in dictating the procedure. It would be desirable to provide a system which is effective for passively receiving voice data in any given arrangement, format, or the like, and generating a formal medical record without extensive and supplemental physician interaction.

BRIEF SUMMARY OF THE INVENTION

In accordance with one aspect of the present invention, a hosted "smart" electronic health record (EHR) system and method are provided for facilitating healthcare quality by increasing the amount of information available to healthcare providers at the point of care and the amount of time that said providers have available to spend interacting directly with patients.

In an embodiment of a system in accordance with the present invention, a mobile application in tandem with a wireless microphone collects voice signals during a patient-caregiver encounter, transforms the voice signals into audio data files, and uploads the audio data files to a server-based platform. A speech recognition software module digitally transcribes the audio data file into text. A text processing module extracts and organizes relevant clinical data based on keywords, key phrases, various patterns of words and phrases, and associated question/answer analysis. Relevance of words and phrases may be determined in view of, e.g., their presence, frequency and context. A diagnostic decision support module enables the healthcare provider to review the determined clinical information and provide a diagnosis associated with the encounter. A documentation skeleton module extracts diagnosis-specific text components from the transcribed text file and assembles an electronic medical document based on the diagnosis and the diagnosis-specific text components.

In further aspects within the scope of the present invention, the system may integrate passive voice data collection and server-based analysis with broader automated distribution throughout an associated EHR platform, and further include or otherwise integrate with a Personal Health Record (PHR) system having comprehensive (and real-time) daily tracking, patient education, patient scheduling, practice management, reporting, real-time data access, and analytics functions.

In even further aspects within the scope of the present invention, the system may incorporate or otherwise integrate an interface or platform for automated scheduling and coding assistance for billing and other encounter-based or home-health tracking functions.

DETAILED DESCRIPTION OF THE INVENTION

With reference generally to FIGS. 1-4, various embodiments of a system and method in accordance with the present invention may now be described herein. Briefly stated, a server-based and web-integrated system and associated methods are provided for improving provider efficiency and accordingly the quality of healthcare.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may. Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

Figure 1:
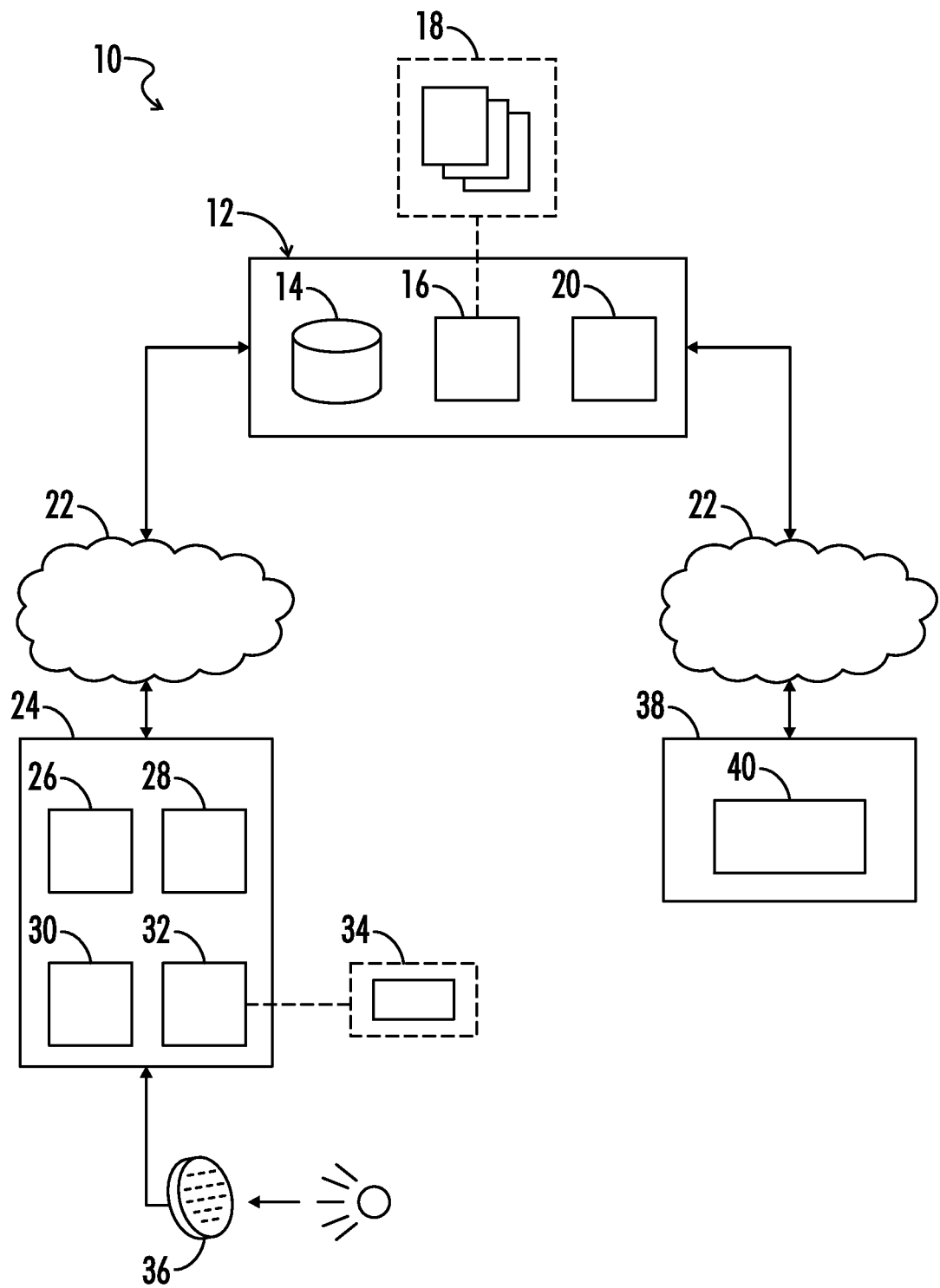
FIG. 1 is a block diagram representing a system in an exemplary embodiment of the present invention.

Referring first to FIG. 1, a system 10 according to various embodiments of the present invention may typically include a hosted server 12 upon which resides a database 14 and a computer-readable storage medium 16 having a computer program product 18 embodied therein. The term "computer-readable storage medium" as used herein may refer to any non-transitory medium alone or as one of a plurality of non-transitory memory media having processor-executable software, instructions, program modules and the like which upon execution may provide data or otherwise cause a computer system to implement subject matter or otherwise operate in a specific manner as further defined herein. It may further be understood that more than one type of memory media may be used in combination to conduct processor-executable software, instructions, program modules, etc., from a first memory medium upon which the software, instructions, program modules and the like initially reside to a processor 20 for execution.

"Memory media" may unless otherwise stated further include without limitation transmission media and/or storage media. "Storage media" may refer in an equivalent manner to volatile and non-volatile, removable and non-removable media, including at least dynamic memory, application specific integrated circuits (ASIC), chip memory devices, optical or magnetic disk memory devices, flash memory devices, or any other medium which may be used to stored data in a processor-accessible manner, and may unless otherwise stated either reside on a single computing platform or be distributed across a plurality of such platforms. "Transmission media" may include any tangible media effective to permit processor-executable software, instructions or program modules residing on the media to be read and executed by a processor, including without limitation wire, cable, fiber-optic and wireless media such as is known in the art.

The server 12 may further include transactional and/or informational databases, I/O modules, user interfaces, and the like as may for example be incorporated within, associated with, or otherwise generated by the program product in accordance with the below-referenced method steps. Such interfaces may include but are not limited to web pages, individually or as collectively defining a hosted website, for providing user (physician) access to health records generated by or otherwise stored in association with the host system, receiving user (physician) input regarding diagnoses or other pertinent information with respect to methods of the present invention, for providing user (patient) access to personal health records (PHR), or any other equivalent or functionally related uses as may be anticipated by one of skill in the art. Such interfaces may in a broader sense include pop-ups or links to third party websites for the purpose of further accessing and/or integrating associated materials, data or program functions via the hosted system and in accordance with methods of the present invention.

The system may further include various devices 24, 38 capable of gathering or displaying data and bi-directionally communicating the data with respect to the hosted server 12 via a communications network 22. The term "communications network" as used herein with respect to data communication between two or more parties or otherwise between communications network interfaces associated with two or more parties may refer to any one of, or a combination of any two or more of, telecommunications networks (whether wired, wireless, cellular or the like), a global network such as the Internet, local networks, network links, Internet Service Providers (ISP's), and intermediate communication interfaces.

In various embodiments some or all of the devices may include program modules (e.g., code snippets or mobile applications) associated with the computer program product and individually executable to perform one or more of the method steps recited herein.

In certain embodiments a hosted system may include more than one server having components functionally linked via a communications network for collective execution of the method steps recited herein. Alternatively or supplemental to such embodiments, the hosted system may include software-as-a-service (SAAS) or equivalent cloud-based program products, databases, and the like which are effective to function alongside the hosted server-based applications and components.

In additional embodiments, a hosted system may effectively communicate with and incorporate or otherwise functionally link to third-party websites and/or databases. As one example, decision support data, evidence-based literature and reference data, patient documentation, etc., residing on or otherwise stored with respect to a third-party platform may be accessed by the host system in accordance with a voice data transcription, physician diagnosis, or the like, and incorporated into a formal record within the scope of the present invention, in an equivalent manner as to where such data is otherwise stored in the hosted system.

Referring again to FIG. 1, in an embodiment the host server 12 interacts with a computing device 24 such as for example a mobile computing device (e.g., a smart phone) having a processor 26, a display unit 28, a process actuator 30 such as for example an RFID transceiver, and a computer-readable storage medium 32 which may further include a mobile application or equivalent software modules effective upon execution by the processor 26 to carry out certain steps according to the present invention. As an alternative to mobile application instructions residing locally on the device 24, as mentioned above the device 24 may be capable of executing remotely stored instructions as may direct the performance of certain steps according to the present invention.

The mobile computing device 24 may include or otherwise communicate with an audio input device 36 such as a microphone. Such communication may preferably be wireless (e.g., via Bluetooth technology), but may within the scope of the present invention may implement a wired connection or even an integral component with respect to the mobile computing device 24 itself.

A user interface 40 may further be generated by program modules 18 executed from the server 12 and accessible from a server or computing device 38 associated with a healthcare provider/caregiver according to methods of the present invention, or alternatively the user interface 40 may be generated by program modules 18 or code snippets residing upon and executable from the healthcare provider server or device 38 itself.

Figure 2:
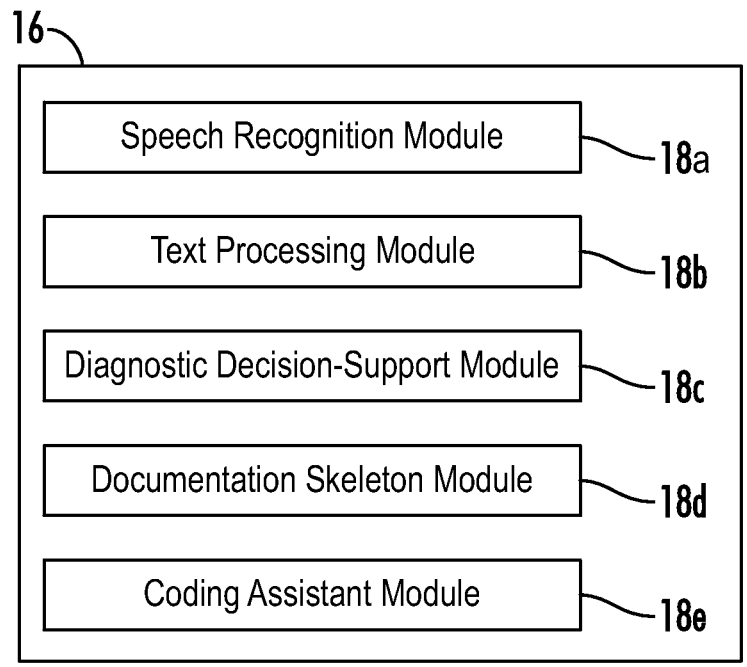
FIG. 2 is a block diagram representing exemplary server-based program modules in the embodiment of FIG. 1.

Referring now to FIG. 2, in an exemplary embodiment the server-implemented program instructions 18 define a plurality of program modules including a speech recognition module 18a, a text processing module 18b, a diagnostic decision-support module 18c, a documentation skeleton module 18d, and a coding assistant module 18e, details for each of which may be provided below. It may be understood that the modules as recited herein relate primarily to an associated function performed upon execution, and that one or more modules may be integrated to collectively perform a number of functions, that one or more modules may be removed from the system for particular applications, and further that additional modules may be defined and implemented as needed or desired in accordance with embodiments of the present invention.

It may be further understood by a person having ordinary skill in the art that a number of algorithms, templates (document skeletons), analytics criteria, key words, key phrases, etc., may be provided and combined to implement the steps and features further described below, and that a single recited example should not be taken as limiting on the scope of the present invention unless otherwise stated. The term "phrase" as used herein may refer generally to a particular string of words, or alternatively to a single word used in a particular context or otherwise in association with any one of a plurality of predefined word groupings so as to meet clinical pre-processing criteria according to embodiments of the present invention.

Figure 3:
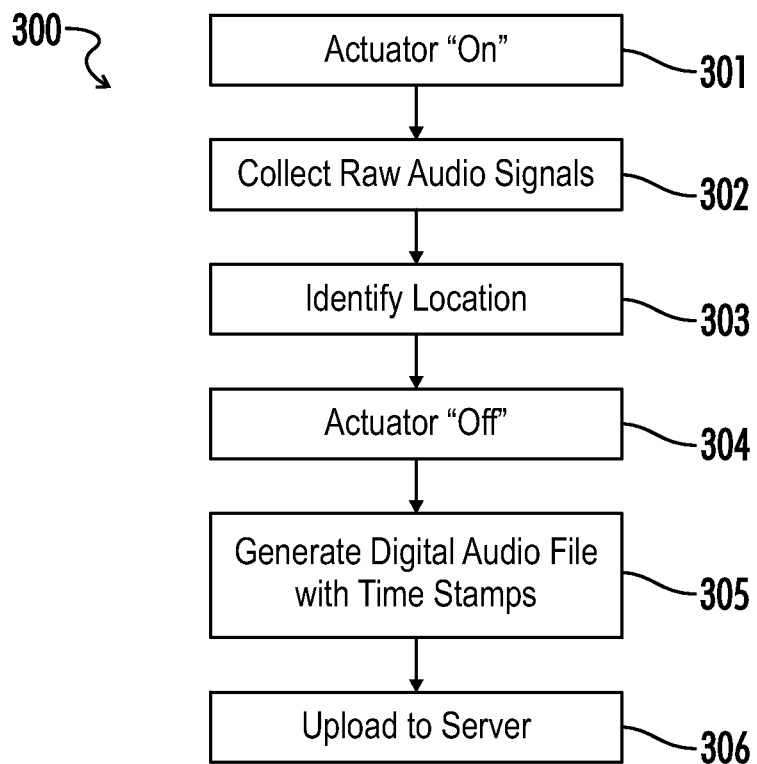
FIG. 3 is a flowchart representing a first stage of an exemplary method of an embodiment of the present invention as executed from a mobile computing platform.

Referring now to FIG. 3, an exemplary process 300 may now be described for collecting voice data from a patient-physician encounter. The term "encounter" as used herein may refer to without limitation to any medical interviews, examinations, procedures, follow-ups and the like.

The exemplary voice data collection process 300 begins with the actuation of voice data transmission and recording, typically at least prior to the beginning of the encounter (step 301). In an embodiment the voice data transmission may be accomplished using a Bluetooth wireless headset with microphone and a computing device having software compatibility to receive signals from the microphone.

Actuation may be accomplished manually via for example a Bluetooth microphone toggle, or user manipulation of a button or the like on a user interface generated by the computing device.

Alternatively, actuation may be automatically accomplished through the use of wireless proximity detection with respect to the patient and the healthcare provider associated with the encounter at issue. Each of the patient and the provider may for example be provided with an RFID transceiver, wherein upon detecting that each party is within a predetermined distance with respect to the other, an actuator is automatically toggled "on."

Software executed from the computing device, which may be a resident computing device with respect to the room in which the encounter is taking place but may preferably be a mobile computing device associated with the healthcare provider, collects raw audio signals during the patient encounter (step 302). The user interface of the computing device may be configured to provide an audio visualization indicator in the form of a small animated graphic, a colored icon, a digital timer, or the like so as to confirm that audio is being gathered by the system.

In various embodiments the software may further identify a location of the encounter using for example a GPS receiver associated with the computing device (step 303). One advantage to identifying the location may be storing the audio signals in association with the location for the purpose of confirming the identity of the patient in that encounter. Another feature which may be useful for this purpose among others is a camera actuator, wherein the user may take a picture of the patient or some portion of the patient and the software directs storage of an image file in association with the particular encounter. The audio, location and image file may be independently reviewable by a user as attachments to the encounter, and further may be extracted for inclusion in an electronic health record as further described below.

At some point, the healthcare provider and/or patient will leave the room or otherwise separate from each other, at which time the RFID transceivers indicate an end of the encounter, and the actuator is automatically toggled "off" to disable the voice data collection (step 304).

Software executed from the local computing device further generates a digital audio file from the raw audio signals (step 305), and in various embodiments may further implement a local audio collection timer to provide time stamps in association with portions of the digital audio file. In one example, the beginning and ending times of a particular audio file may be documented along with time elapsed from the beginning of the audio. Alternatively, a real time stamp may be applied concurrently with the audio recording and without reference to the start time. The computing device may then automatically, or manually in response to user actuation (e.g., a "send" command via a user interface generated on the device display), upload the audio file to the host server for subsequent processing and analysis (step 306). In certain embodiments, audio uploading may occur in segments during an encounter, rather than all audio after the conclusion of the encounter.

Figure 4:
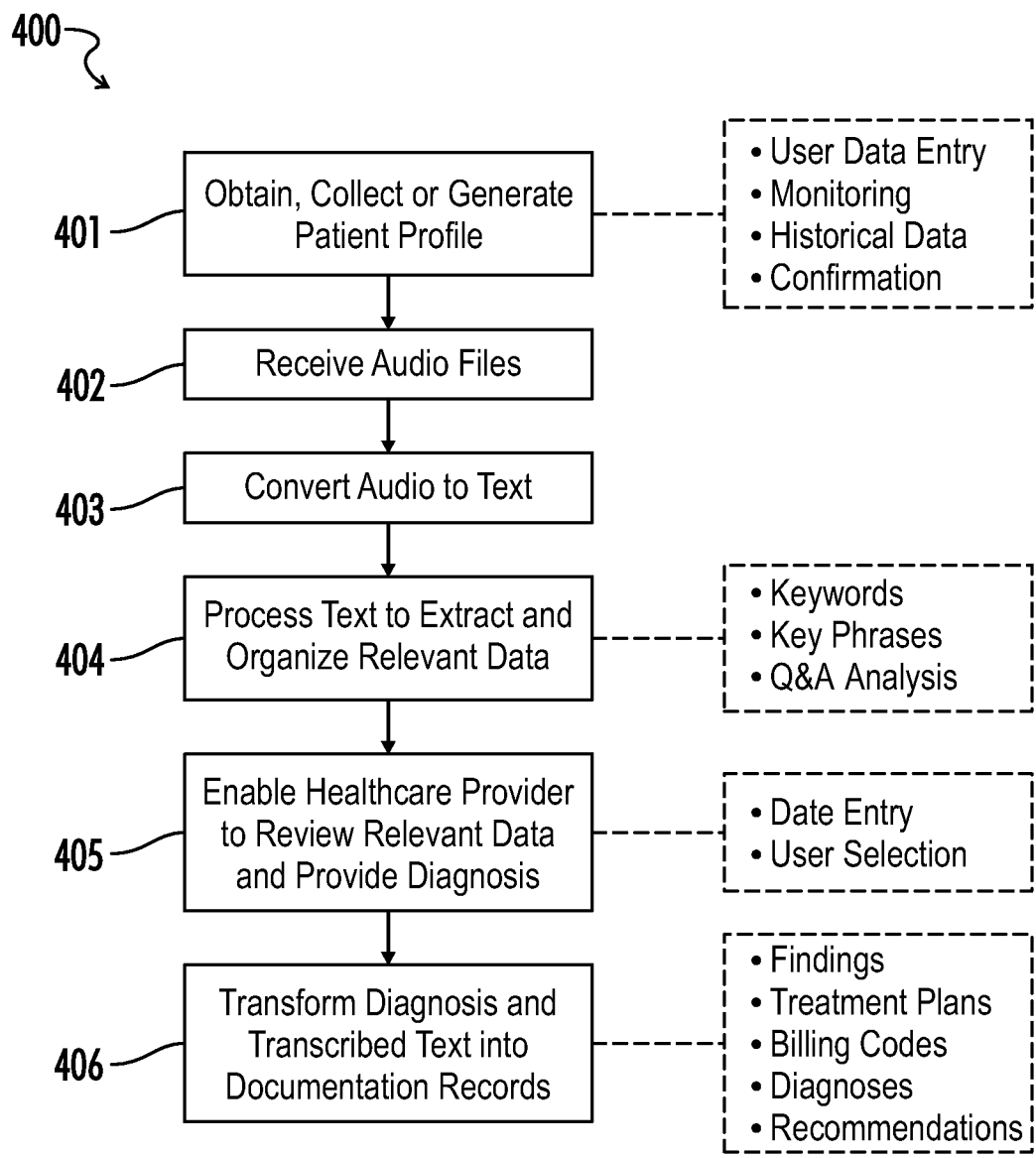
FIG. 4 is a flowchart representing a second stage of an exemplary method of an embodiment of the present invention as executed from a web-accessible server platform.

Referring now to FIG. 4, an exemplary process 400 as executed in accordance with embodiments of the present invention from a server-based platform may now be described.

With respect to a particular patient, the system may typically as a preliminary step obtain, collect or generate data as needed to provide a patient profile (step 401). A preliminary differential diagnosis may further be provided based at least in part on the patient profile, and further depending on the context may be based on direct user input such as for example a primary complaint. The profile itself may be generated based on direct user input (primary complaints, trends, question and answer), historical data with respect to previous user input or as for example collected from third party data sources, user activity data such as may have been collected over time via ambulatory monitoring, or the like. In various embodiments a decision support system may be utilized to streamline the data entry and retrieval process, and may further confirm the validity of data points such as for example by cross-checking variables and identifying conflicts in input data.

With respect to a particular encounter associated with the patient, the server receives an audio file that has been uploaded from the mobile (or otherwise local with respect to the encounter itself) computing device (step 402). A speech recognition program module may be implemented to transcribe the collected and stored audio into a text file (step 403). Such a step may generally be implemented using any one or more of various third party software tools as are known in the art, and further discussion of the technical aspects of the voice transcription step may accordingly be omitted herein.

A text processing module associated with the server system may subsequently be implemented to extract and organize relevant data from the transcribed text file (step 404). Generally stated, the transcription is parsed for keywords, key clinical phrases, and other key elements or text components, and the rules-based analysis may be guided for example using the preliminary diagnosis described above, detected questions and answers from the text, corresponding keywords and phrases, etc.

In determining the relevance or value of clinical information to be collected from the transcription, the text processing module may access and implement rules engines and one or more databases including predetermined keyword associations, medical and pharmaceutical records, contra-indications, patient profiles, etc.

In one example of a step to implement a core functionality of the text processing step according to the present invention, the program module directs the processor to identify the presence of one or more predetermined keywords in the text file based on for example the preliminary diagnosis, and to categorize associated keyword elements. Exemplary categories or "buckets" may include without limitation: demographics; allergies; observed or reported symptoms; current or historical medications; procedures; physical or mental problems, conditions or diseases; labs and radiology orders; referrals; etc.

In another example, the text processing module may direct the performance of key-phrase analysis wherein the system picks up certain key predetermined clinical phrases and attempts to determine or score their value or relevance. The value or relevance of a particular phrase may vary in predetermined manners according to use of the phrase in the context of a particular preliminary diagnosis, or in the context of other questions and answers with respect to that patient or encounter, etc. Alternatively, the value or relevance of a particular phrase may be weighted according to particular conditions associated with that patient or encounter, such weighting applied according to rules-based algorithms or machine learning engines executed by the system within the scope of the present invention.

A basic process for scoring the relevance of keywords and phrases from the text file may typically include some form of Counter for identifying a number of times that the keywords and clinical phrases are used during the encounter, further processed in view of their timing, frequency, context, etc.

An exemplary methodology for scoring the relevance of a predetermined key clinical phrase may include identifying time stamps associated with each use of the key clinical phrase and applying a value to the phrase based on a number of uses of the phrase during a period of time based on the time stamps. For example, having identified a first use of a predetermined phrase, the system may tag the first use and determine a lapsed amount of time between the first use and a second use of the same phrase. If the lapsed time is determined to be less than a threshold amount of time, the text processing module may ascribe a certain amount of additional weighting to that phrase, potentially further in view of that phrase's inherent relevance to the preliminary diagnosis itself.

Another exemplary methodology may include identifying time stamps associated with each use of a key clinical phrase and weighing the phrase based on the associated time stamp and a location of the phrase with respect to a predetermined block of time during the encounter. As but one example, all keywords or phrases identified in a second half of the encounter may be counted twice per occurrence with respect to such keywords or phrases in a first half of the encounter.

Yet another example may include identifying a "trigger" text component within a predetermined number of words or within a predetermined amount of time with respect to the phrase. For example, if "yes" or a synonym of "yes" is spoken within three words of a predetermined keyword or clinical phrase (as may be applied forwards or backwards with respect to the keyword or clinical phrase), then the value or relevance of the keyword or clinical phrase may be counted three times in the Counter to increase its relative "rank."

In various embodiments of the present invention, an automated diagnostic decision support program module may be executed (step 405) to generate a web-accessible user interface which enables the healthcare provider to review relevant terms, data, and the like and further to choose an appropriate diagnosis and diagnosis code for the patient. The user interface may simply present a data entry field within which the healthcare provider types in or otherwise provides a diagnosis and diagnosis code (or a series of diagnoses and codes), or alternatively the user interface may provide a list of codes and diagnoses from which the healthcare provider may simply select one or more in association with the patient. The list of provided codes and diagnoses may be determined according to for example the most relevant or most highly valued keywords and clinical phrases from the text processing module. The healthcare provider may be enabled to click various listed codes and diagnoses for the purpose of expanding the scope of available display information and "drilling down" into the relevant data sources in accordance with well-known decision support tools.

A documentation skeleton module may further be executed (step 406) to transform the primary diagnosis and portions of the transcribed text into a documentation record. Diagnosis code-specific terms, phrases, findings, etc., may be extracted from pre-processed Buckets associated with the transcribed text based on a pre-defined diagnosis-specific dictionary of symptoms, signs/physical examination findings, pertinent historical information such as labs and radiologic studies, treatment plans, billing codes and the like. The extracted terms, etc., may be presented in a prioritized manner, while the remaining diagnosis-specific dictionary options are further presented or searchable for user selection and adding modifiers.

The Documentation Skeleton may include diagnosis-specific sections including but not limited to for example a primary complaint, encounter narrative, symptoms, past/current medical history, past surgical history, family history, social history, past/current medications, vital signs, physical exam results, laboratory data, radiological data and treatment plans.

Treatment plans may be presented by diagnosis or problem, particularly is there are secondary and tertiary diagnoses, like chronic diseases, complex patients, etc. Recommendations may be provided in the form of free text input plus imported text that describes directions or instructions for the patient to follow (e.g., "Try to eat more fresh veggies at least 3× per week," "Return to the clinic or emergency department immediately if bleeding continues," etc.). The treatment plans may further include automatically recommended medication prescriptions, laboratory orders, radiological orders and/or specialist referrals pertinent to the primary diagnosis (or combination of diagnoses).

The extracted terms, keywords, phrases, etc., may be mapped to components such as the findings, treatment plans, recommendations, billing codes, etc., to further populate the comprehensive document skeleton.

In an embodiment, each diagnosis-specific section that has pre-filled data may be displayed as bolded and underlined relative to those sections for which no data was fed into from the database/record. For example, if a past disease was picked up in the audio record, the past/current medical history (PMH) would be bold, but if no medications were picked up in the audio record that section would not be bold, etc. Once a particular component is clicked by a user, a javascript-based fly-out window may appear displaying the data, with each data point having for example an indicator such as a small "x" accompanying it in case the provider wants to remove that data point. Each component may further have a free-text input component that automatically searches the remainder of the patient's record as the user types letters (character-by-character search) to find appropriate matches, first from the patient profile and then against larger component-specific databases.

The document skeleton may include multiple diagnoses where applicable, as may be provided in visually distinct layers or otherwise as may be conflated where appropriate. For example, relevant requisite data fields may be combined for ease of display and user processing with respect to each additional (secondary and tertiary/chronic) diagnosis that is provided.

In certain embodiments, a host system of the present invention may support additional functionality which may be introduced as part of a web services-based application platform using standards-based protocols. For example, server-based program modules may enable a range of third party web-based and mobile applications and systems integration, including but not limited to mobile health applications and home health monitors (e.g., blood glucose meter, scale, home blood pressure cuff, etc.), facilitating an interactive and collaborative patient healthcare record. The server-based patient record can be passively and continuously or periodically stored, backed-up and updated via a dedicated update "tunnel" regardless of the physical location of the patient and associated devices. Further, a web-accessible user interface associated with the host system may facilitate patient interaction and collaboration with respect to reducing encounter time or the amount of time spent in the healthcare facility, such as for example by enabling access to healthcare information, remote check-ins and appointment preparation, and user entry of preliminary information such as complaints, symptoms, recent activity and medications, other Q&A, etc. Such data entry can be processed not only by healthcare administrators with respect to making appointments and handling preliminary paperwork, but can also be directly integrated into a patient profile and used to generate preliminary diagnoses as further described above with respect to steps of the various processes of the present invention.

The previous detailed description has been provided for the purposes of illustration and description. Thus, although there have been described particular embodiments of the present invention of a new and useful "Electronic Health Record System and Method of Patient Encounter Transcription and Documentation," it is not intended that such references be construed as limitations upon the scope of this invention except as set forth in the following claims.

What is claimed is:

1. A system comprising:
one or more databases including patient profile data generated based on one or more of direct input from a patient and historical data associated with the patient;
a first wireless proximity sensor associated with the patient and a second wireless proximity sensor associated a healthcare provider;
a mobile computing device comprising a first processor and a first non-transitory computer-readable storage medium having program instructions residing thereon, the instructions in the first storage medium executable by the first processor to direct the performance of operations comprising
receiving a first signal from one or more of the first and second wireless proximity sensors representing that the healthcare provider is within a predetermined distance with respect to the patient,
upon receiving the first signal, actuating voice signal collection for an encounter between the patient and a healthcare provider,
passively collecting voice signals associated with the patient and the healthcare provider during the encounter via a microphone communicatively linked to the first processor,
receiving a second signal from one or more of the first and second wireless proximity sensors representing that the healthcare provider has exceeded a predetermined distance with respect to the patient,
upon receiving the second signal, disabling voice signal collection for the encounter based on a second input from the one or more process actuators,
transforming the voice signals into one or more audio data files,
uploading the audio data file to a host server via a communications network;
said host server comprising a second processor and a second non-transitory computer-readable storage medium having program instructions residing thereon, the instructions in the second storage medium executable by the second processor to direct the performance of operations comprising
generating a preliminary diagnosis based on the patient profile data,
digitally transcribing the audio data file into a text file format,
determining relevant clinical information based on contextual analysis of the transcribed text file based on the preliminary diagnosis,
generating a user interface displaying a list of diagnoses and diagnosis codes associated with the encounter as determined according to the relevant clinical information,
via the generated user interface, enabling the healthcare provider to review the determined clinical information and provide a primary diagnosis associated with the encounter,
extracting primary diagnosis-specific text components from the transcribed text file, and
assembling an electronic medical document based on the primary diagnosis and the primary diagnosis-specific text components.

2. The system of claim 1, wherein the step of determining relevant clinical information comprises identifying the presence of one or more predetermined keywords in the transcribed text file and categorizing associated keyword elements based on the preliminary diagnosis.

3. The system of claim 2, wherein the step of determining relevant clinical information further comprises identifying the presence of one or more predetermined key clinical phrases in the text file and scoring the relevance of the phrases.

4. The system of claim 3, wherein scoring the relevance of a predetermined key clinical phrase comprises identifying time stamps associated with each use of the key clinical phrase and applying a value to the phrase based on a number of uses of the phrase during a period of time based on the time stamps.

5. The system of claim 3, wherein scoring the relevance of a predetermined key clinical phrase comprises identifying time stamps associated with each use of the key clinical phrase and weighing the phrase based on the associated time stamp and a location of the phrase with respect to a predetermined block of time during the encounter.

6. The system of claim 3, wherein scoring the relevance of a predetermined key clinical phrase comprises identifying a trigger text component within one or more of a predetermined number of words and a predetermined amount of time with respect to the phrase.

7. The system of claim 1, wherein the proximity sensors comprise a first transceiver associated with the patient and a second transceiver associated with the healthcare provider.

8. The system of claim 1, the instructions from the host server further executable by the second processor to direct the generation of a web-accessible user interface wherein inputs from patient data entry and patient monitoring devices are integrated with profile data for a respective patient in the one or more databases.

9. A method of passive voice data collection and medical profile transformation, the method comprising the steps of:
    generating a preliminary diagnosis based on patient profile data comprising one or more of direct input from a patient and historical data associated with the patient;
    providing a first signal from one or more of a plurality of wireless proximity sensors representing that a healthcare provider is within a predetermined distance with respect to the patient;
    upon receiving the first signal, actuating voice signal collection for an encounter between the patient and the healthcare provider;
    collecting analog voice signals associated with the patient and the healthcare provider during the encounter;
    providing a second signal from one or more of a plurality of wireless proximity sensors representing that the healthcare provider is no longer within a predetermined distance with respect to the patient;
    upon receiving the second signal, disabling voice signal collection for the encounter based on a second input from the one or more process actuators;
    digitally transforming the voice signals into a text file format;
    determining relevant clinical information based on contextual presence and usage of one or more predetermined text components in the text file, based on the preliminary diagnosis;
    generating a user interface displaying a list of diagnoses and diagnosis codes associated with the encounter as determined according to the relevant clinical information;
    via the generated user interface, enabling the healthcare provider to review the determined clinical information and provide a primary diagnosis associated with the encounter;
    extracting primary diagnosis-specific text components from the transcribed text file; and
    assembling an electronic medical document based on the primary diagnosis and the primary diagnosis-specific text components.

10. The method of claim 9, wherein the step of determining relevant clinical information comprises identifying the presence of one or more predetermined keywords in the text file and categorizing associated keyword elements based on the preliminary diagnosis.

11. The method of claim 10, wherein the step of determining relevant clinical information further comprises identifying the presence of one or more predetermined key clinical phrases in the text file and scoring the relevance of the phrases.

12. The method of claim 11, wherein scoring the relevance of a predetermined key clinical phrase comprises identifying time stamps associated with each use of the key clinical phrase and applying a value to the phrase based on a number of uses of the phrase during a period of time based on the time stamps.

13. The method of claim 11, wherein scoring the relevance of a predetermined key clinical phrase comprises identifying time stamps associated with each use of the key clinical phrase and weighing the phrase based on the associated time stamp and a location of the phrase with respect to a predetermined block of time during the encounter.

14. The method of claim 11, wherein scoring the relevance of a predetermined key clinical phrase comprises identifying a trigger text component within one or more of a predetermined number of words and a predetermined amount of time with respect to the phrase.

15. The method of claim 9, further comprising integrating patient data entry inputs from a web interface with profile data for a respective patient.

16. The method of claim 9, further comprising integrating patient activity monitoring device inputs from a web interface with profile data for a respective patient.

17. The method of claim 9, further comprising integrating patient home health monitoring device inputs from a web interface with profile data for a respective patient.

* * * * *